United States Patent
Snowden

(10) Patent No.: US 6,214,373 B1
(45) Date of Patent: Apr. 10, 2001

(54) NUTRITIONAL COMPOSITION FOR TREATING INFLAMMATORY BOWEL DISEASES

(75) Inventor: Robert B. Snowden, Churchville, PA (US)

(73) Assignee: Snowden-Sutton Associates, Inc., Churchville, PA (US)

(*) Notice: Subject to any disclaimer, the term of this patent is extended or adjusted under 35 U.S.C. 154(b) by 0 days.

(21) Appl. No.: 09/414,666

(22) Filed: Oct. 7, 1999

(51) Int. Cl.⁷ .................................................. A61K 47/00
(52) U.S. Cl. ........................ 424/439; 424/400; 424/442; 424/451; 424/464; 424/465
(58) Field of Search .................................... 424/400, 439, 424/442, 451, 464, 465

(56) References Cited

U.S. PATENT DOCUMENTS

| | | |
|---|---|---|
| 4,587,793 | 5/1986 | Brennan et al. . |
| 4,617,317 | 10/1986 | Bennet . |
| 4,806,354 | 2/1989 | Green . |
| 5,135,918 | 8/1992 | Peraita . |
| 5,292,538 | 3/1994 | Paul et al. . |
| 5,405,613 | 4/1995 | Rowland . |
| 5,472,957 | 12/1995 | Hesse et al. . |
| 5,494,678 | 2/1996 | Paradissis et al. . |
| 5,578,576 | 11/1996 | Leddin . |
| 5,780,451 | * 7/1998 | DeMichele et al. ............... 514/54 |

OTHER PUBLICATIONS

Harrison's Principles of Internal Medicine, 12th Ed., vol. 2, McGraw–Hill, Inc., pp. 1268–1281, 1991.

Franklin, et al., Impaired Folic Acid Absorption in Inflammatory Bowel Disease: Effects of Salicylazosulfapyridine (Azulfidine), vol. 64, No. 4, Gastroenterology, pp. 517–525, Apr. 1973.

Linaker, Scurvy and Vitamin C Deficiency in Chron's Disease Postgraduate Medical Journal (Jan. 1979), vol. 55, pp. 26–29.

Nugent, et al., Malignant Potential of Chronic Ulcerative Colitis, American Gastroenterology Association, 1979, vol. 76(1), pp. 1–5.

Penny, et al., Relationship Between Trace Elements, Sugar Consumption, and Taste in Chron's Disease, Gut. 1983, vol. 24, pp. 288–292.

McClain, et al., Zinc–Deficiency–Induced Retinal Dysfunction in Chron's Disease, Digestive Diseases and Sciences, vol. 28, No. 1 (Jan. 1983), pp. 85–87., ",".

Harries, et al., Nutritional Disturbances in Chron's Disease, Postgraduate Medical Journal (Nov. 1983), vol. 59, pp. 690–697.

FernandezBanares, et al., Vitamin Status in Patients with Inflammatory Bowel Disease, The American Journal of Gastroenterology, vol. 84, No. 7, 1989, pp. 744–748.

Vogelsang, et al., Bone Disease in Vitamin D–Deficient Patients with Chron's Disease, Digestive Diseases and Sciences, vol. 34, No. 7 (Jul. 1989), pp. 1094–1099., ",".

Recommended Dietary Allowances, 10th Ed., National Academy Press, Washington, DC 1989, "Fat–Soluble Vitamins", pp. 78–92, "Water–Soluble Vitamins", p. 115, pp. 169–185, pp. 212–217.

Ivey, et al., Nutritional Supplement, Mineral, and Vitamin Products, "Handbook of Nonprescription Drugs", 9th Ed., American Pharmaceutical Association, 1990, pp. 447–480.

Heatley, Assessing Nutritional State in Inflammatory Bowel Disease, Gut 1986, vol. 27, S1, pp. 61–66.

Collins, et al., Colon Cancer, Dysplasia, and Surveillance in Patients with Ulcerative Colitis, The New England Journal of Medicine, Jun. 1987, vol. 316, pp. 1654–1658.

Nakamura, et al., Zinc Clearance Correlates with Clinical Severity of Chrons's Disease a Kinetic Study, Digestive Diseases and Sciences, vol. 33, No. 12 (Dec. 1988) pp. 1520–1524.

Sturniolo, et al., Zinc Absorption in Chron's Disease, Gut, 1980, vol. 21, pp. 387–391.

Lashner, et al., Effect of Folate Supplementation on the Incidence of Dysplasia and Cancer in Chronic Ulcerative Colitis, Gastroenterology, 1989, vol. 97, pp. 255–259.

Rosenberg, et al., Folate, Dysplasia, and Cancer, Gastroenterology, 1989, vol. 97, pp. 502–503.

Lederle, F., Oral Cobalamin for Pernicious Anemia, Jama, Jan. 1991, vol. 265, No. 1, pp. 94–95.

Hathcock, et al., Oral Cobalamin for Treatment of Pernicious Anemia?, Jama, Jan. 1991, vol. 265, No. 1, pp. 96–97.

* cited by examiner

Primary Examiner—Thurman K. Page
Assistant Examiner—Rachel M. Bennett

(57) ABSTRACT

A nutritional composition and method useful for treatment of inflammatory bowel diseases is disclosed, the composition comprising selected vitamins and mineral salts for oral administration to a subject having an inflammatory bowel disease. The composition comprises an excess of vitamin D and vitamin $B_{12}$, contains vitamin C and iron in quantities promoting good absorption, contains water miscible forms of the fat soluble vitamins, and no phosphate or carbonate salts. Preferably, the iron is present as ferrous fumarate. And, preferably the composition is essentially free of magnesium.

18 Claims, No Drawings

NUTRITIONAL COMPOSITION FOR TREATING INFLAMMATORY BOWEL DISEASES

FIELD OF THE INVENTION

The present invention relates to nutritional compositions for treating subjects having an inflammatory bowel disease. In particular, the nutritional composition of the present invention relates to a composition providing nutrients that supply the unmet needs for nutrition of subjects suffering from an inflammatory bowel disease such as ulcerative colitis or Crohn's disease, or from celiac disease. The invention also provides a new method for treating inflammatory bowel diseases by supplying selected nutrients in a novel composition suitable for peroral administration.

BACKGROUND OF THE INVENTION

The term "Inflammatory Bowel Disease" (IBD) is commonly used to refer to a group of related, but distinct, chronic inflammatory conditions affecting the gastrointestinal tract. Diagnosis of these chronic inflammatory conditions is generally made into one of two groups, Crohn's disease and ulcerative colitis. Both of these disorders involve recurring inflammatory processes within the bowel. Crohn's disease may involve any segment of the gastrointestinal tract, although characteristically the region of greatest involvement is the small bowel and the proximal colon. In ulcerative colitis the inflammation is, by definition, limited to the mucosa of the large bowel. The present invention is concerned with nutritional support for a person having either Crohn's disease or having ulcerative colitis. The present invention provides a new composition for supplying the nutritional needs of subjects afflicted with these disorders. The new composition is also useful for supplying the nutritional needs of subjects with celiac disease. A new method of treating subjects having these disorders is also provided by the present invention, the method for treating the subjects comprising oral administration of the new composition.

Crohn's disease and ulcerative colitis are both believed to involve immune mechanisms. At present, no exact causes for these disorders are known. No cures for these disorders are available either. Subjects afflicted with these disorders are generally treated currently with therapies that are directed at reducing the inflammatory processes in the subjects, and that are directed at reducing the effects of the inflammatory processes in the subjects. Current medical treatment is intended to decrease the number, frequency and severity of acute exacerbations of inflammatory bowel disease and to preventing secondary complications, but at best, the results are disappointing. Immunosuppressant drugs are frequently used for IBD, including sulfasalazine, azathioprine and steroids.

Subjects afflicted with these disorders suffer from chronic nutritional deficiencies because of malabsorption and the poor condition of their gastrointestinal mucosa. These subjects frequently suffer from an inability to properly absorb vitamins and minerals.

Therapeutic methods have been proposed for treating the nutritional needs peculiar to subjects with IBD. These include total parenteral nutrition as well as supplementation of the subject's diet with conventional oral vitamin or mineral supplements. Frequently, these proposed methods are found insufficient to provide adequate nutrition for the subject.

Subjects suffering from IBD have been reported to suffer from a deficiency of iron. It is known that some forms of iron are more easily absorbed from the gastrointestinal tract than are others. The composition of the present invention supplies iron in a form that is easily absorbed by a subject when administered orally. Absorbability of Different Iron Compounds, H. Brise and L. Hallberg, Acta Med. Scand. (Suppl.) vol. 376, 23–37 (1962). Preferably ferrous fumarate is used in the inventive composition to ensure adequate amounts of easily absorbable iron for a subject.

Subjects with an IBD such as Crohn's disease can also suffer from a zinc deficiency. It has been reported that this deficiency can cause abnormalities of the retina. "Zinc-Deficiency-Induced Retinal Dysfunction in Crohn's Disease," C. J. McClain, et al., Digestive Diseases and Sciences, vol. 28, 85–87 (1983). The inventive composition provides zinc in an excess over that provided in conventional vitamin and mineral combinations, and in an amount sufficient to prevent or alleviate the retinal problems associated with IBD.

Subjects suffering from IBD also have a need for increased amounts of vitamin C. "Scurvy and Vitamin C Deficiency in Crohn's Disease," B. D. Linaker, Postgraduate Medical Journal, vol. 55, 26–29 (1979). The inventive composition provides vitamin C in an amount in excess over that provided in conventional multi-vitamin preparations, where the amount is selected to be therapeutic for a subject having IBD.

The composition according to the present invention provides a subject with oral nutritional therapy that is tailored for the particular needs of a subject having IBD. The composition comprises necessary vitamins and minerals. Some of the vitamins and minerals are present in excess over the amounts provided in conventional multi-vitamin preparations that are commercially available. This is because it has been discovered that a subject with IBD has greater needs for particular vitamins or minerals than for others. The inventive composition disclosed here provides this nutritional therapy without the need for administration of individual vitamin preparations in the amounts needed by such subjects. The inventive composition is suited for oral administration to a subject in need of vitamin and mineral therapy due to IBD. That is, the present invention provides a more convenient preparation for nutritional therapy for subjects with IBD than has been previously available.

In particular, the inventive composition has the following preferred excesses of vitamin amounts over conventional multivitamin compositions. Vitamin $B_{12}$ is supplied in the composition at a level that, when the inventive composition is administered to a subject twice daily, provides about 17 thousand percent of the recommended daily value for this vitamin. Vitamins $B_6$ and E are both supplied at about 500 percent of the recommended daily value. Vitamin $B_2$ is supplied at about 590 percent of the recommended daily value. Vitamin $B_1$ is supplied at about 670 percent of the recommended daily value. Vitamin C is supplied at about 333 percent of the recommended daily value. Vitamin D is supplied at about 200 percent of the recommended daily value. The recommended daily value is defined in "Recommended Dietary Allowances," National Academy Press, (1989).

Minerals are supplied with the following deviations from the amounts found in conventional commercial compositions (as administered twice daily). Iron is supplied at about 167 percent of the recommended daily value. And, zinc is supplied at about 150 percent of the recommended daily value. The amount of calcium supplied by the inventive composition is reduced in the inventive composition to supply about 20 percent of the recommended daily value.

The amounts of each vitamin and mineral in the composition disclosed here have been selected to prevent or alleviate the deficiencies for these nutrients that have been found in subjects with ulcerative colitis or Crohn's disease.

The composition provided by the present invention is also useful for treatment of subjects afflicted with celiac disease, also called celiac sprue or gluten enteropathy. Subjects with celiac disease frequently suffer from nutrient deficiencies caused by the malabsorption that results from their functionally impaired intestinal mucosa. The new composition is suited for providing the vitamin and mineral nutrition that these subjects lack. Although such subjects are currently given nutritional supplements, the composition according to the present invention is particularly well suited to providing their nutritional needs. Children with celiac disease are known to be frequently deficient in iron and adults are frequently deficient in folate. The new composition disclosed here is useful for preventing and alleviating the deficiencies in subjects with celiac disease.

Nutritional compositions have been disclosed previously for treating bowel disorders, but the composition disclosed here is significantly different than those previously disclosed. A nutritional composition for treating ulcerative colitis has been disclosed in U.S. Pat. No. 5,780,451 to DeMichele et al. That composition comprised a mixture of an oil blend and a source of indigestible carbohydrate, which is metabolized to short chain fatty acids. The composition of DeMichele is quite different in its constituents than the composition disclosed here, and was intended for enteral nutrition, not oral nutrition. This patent does not teach a composition according to the present disclosure.

A method of treating ulcerative colitis has been disclosed in U.S. Pat. No. 4,617,317 to Bennet. The method disclosed comprised administration of vitamin K antagonists, particularly derivatives of tocopherol. This patent does not teach a composition or method according to the present disclosure.

A method and composition for treating intestinal wounds or ulcers were disclosed in U.S. Pat. No. 5,578,576 to Leddin. The composition disclosed in that patent comprised certain protein sources, carbohydrates and oils, in a mixture intended for enteral administration. This patent does not teach a composition or method according to the present disclosure.

An unmet need exists therefore for a composition and method useful for treating a subject having an IBD or celiac disease.

To satisfy the outstanding needs outlined above I have now discovered a new nutritional composition. I have also discovered a new method for using this composition for treatment of a subject by oral administration of the inventive composition.

SUMMARY OF THE INVENTION

Briefly, the invention is a nutritional composition for treating subjects having an inflammatory bowel disease or celiac disease.

I have developed a new nutritional composition, useful for peroral treatment of subjects having an inflammatory bowel disease such as Crohn's disease or ulcerative colitis. The new nutritional composition combines in a mixture, selected vitamins in proportions that make the composition especially well suited for treating such subjects. The composition also includes selected minerals in proportions that are also especially well suited for treating these subjects. Preferably, the minerals are present in the composition as salts that will neither give rise to, nor promote the formation of gas in the subject's digestive system.

In addition, the composition according to the present invention provides the subject with water-miscible forms of the fat soluble vitamins A, D, E and K to allow better absorption and utilization of these vitamins by the subject.

It is an aspect of the invention to provide a multivitamin composition especially well suited for treatment of subjects having an inflammatory bowel disease, when the composition is administered by mouth.

It is another aspect of the invention to provide a mineral composition especially well suited for treatment of subjects having an inflammatory bowel disease, when the composition is administered by mouth.

It is an aspect of the invention to provide a combined multivitamin and mineral composition, that is especially well suited for preventing or alleviating nutritional deficiencies of subjects having an inflammatory bowel disease, when the composition is administered by mouth.

It is an aspect of the invention to provide a combined multivitamin and mineral composition, that is especially well suited for treatment of subjects having an inflammatory bowel disease, where the composition is essentially free of magnesium.

It is another aspect of the invention to provide a mineral composition especially well suited for treatment of subjects having an inflammatory bowel disease where the salts present in the composition neither give rise to, nor promote the formation of gas in the digestive system of the subject.

It is yet another aspect of the invention to provide a method of treating a subject having an inflammatory bowel disease where the subject is provided with complete nutritional support in a unit dosage form.

Still another aspect of the invention is to provide a method for preventing or alleviating the particular deficiencies of vitamins and minerals of a subject having an inflammatory bowel disease where the method uses a unit dosage form that may be taken orally by the subject.

Still another aspect of the invention is to provide a method of treating a subject having an inflammatory bowel disease where the subject is provided with complete nutritional support in a unit dosage form that is taken orally, and that need be taken no more than twice daily.

Another aspect of the invention is to provide a composition and method for preventing or alleviating the particular deficiencies of vitamins and minerals of a subject with celiac disease.

These aspects, and others set forth more fully below are achieved by the present invention. In particular, a new composition is disclosed that reduces gas formation in the bowel of a subject, that avoids causing diarrhea in the subject, and that has a vitamin and mineral profile especially suited for providing therapeutic nutrition to subjects having an inflammatory bowel disease.

DETAILED DESCRIPTION OF THE INVENTION

I have developed a new nutritional composition, useful for treating subjects having an inflammatory bowel disease such as Crohn's disease or ulcerative colitis. The new nutritional composition combines in a mixture, selected vitamins in proportions that make the composition especially well suited for treating such subjects. The composition also includes selected minerals in proportions that are also especially well suited for treating these subjects. The minerals are preferably present in the composition as salts that will neither give rise to, nor promote the formation of gas in the subject's digestive system.

An oral multinutrient composition is provided, specially formulated to meet the special nutritional needs of individuals who do not obtain sufficient quantities of certain of the essential vitamins and minerals from their diet. The composition has been formulated to meet the particular needs of subjects who have inflamed gastrointestinal mucosa, and resulting poor absorption or increased excretion of nutrients, or who are on severe dietary restrictions; as in gastrointestinal conditions such as inflammatory bowel disease (IBD) or celiac disease. The composition contains water-miscible forms of the fat soluble vitamins A, D, E and K to enable better absorption and utilization of these vitamins. Vitamin D, important for maintaining bone mass, is supplemented at 2 times the Daily Value, since it is not optimally absorbed by subjects having IBD, and may be inhibited by steroids used in the treatment of IBD.

The new composition contains vitamin C and iron in the ratio and quantities shown to increase iron absorption when given together. Iron is preferably provided as ferrous fumarate, which is highly soluble in the gastrointestinal tract, is well tolerated orally, and was less toxic than ferrous sulfate or ferrous gluconate in laboratory studies. The composition contains folic acid, the daily administration of which has been found in a number of studies to be associated with a reduced risk for the development of colorectal cancer or dysplasia in individuals with ulcerative colitis. The composition preferably contains about 1000 mcg (micrograms) of vitamin $B_{12}$ (cyanocobalamin). Vitamin $B_{12}$ may be poorly absorbed in patients with IBD, particularly in extensive Crohn's disease.

The new composition contains zinc, important for wound healing and immune function, which is supplemented at about 150% of the recommended daily value because it may be lost through increased excretion in individuals with IBD. The composition contains calcium diphosphate, a "non-gassy" or non-carbonate form of calcium. Conventional mineral supplements usually contain calcium carbonate, which can cause gas evolution that can exacerbate diarrhea and create discomfort in subjects with IBD.

The new composition preferably contains essentially no magnesium in either the nutritional ingredients themselves or in any excipients used in a unit dosage form. This is because magnesium can act as a cathartic in subjects having IBD.

The new composition is preferably lactose free, and preferably contains no sugar, colorant, artificial sweetener or flavoring.

It is preferred that the inventive composition be administered orally in a solid unit dosage form such as a tablet, a caplet, or a capsule. The preferred dosage for use in adults is two unit dosage forms daily in a single or divided dose. The preferred dosage for children under the age of 12 may be selected by a physician. The tablet, caplet or capsule may also comprise a pharmaceutically acceptable excipient. Some examples of excipients that are suitable for use in practicing the invention include, but are not limited to the following: carboxymethylcellulose, microcrystalline cellulose, starch, and modified starch.

The inventive composition can also be formulated as a liquid for oral administration. In this case the composition would be formulated as an oral solution. liquid formulations may also comprise pharmaceutically acceptable diluents and additives such as glycerin, sorbitol, mannitol, maltitol, propylene glycol; and aqueous solutions of these Whether the inventive composition is in a solid dosage form or is in a liquid dosage form, the formulation of the dosage form is preferably a pharmaceutically acceptable formulation. Any additional constituents other than the vitamins and minerals claimed here should be ones that are approved for pharmaceutical use by a government regulatory agency, such as the United States Food and Drug Administration.

It is to be understood that the composition and method of this will have utility for non-human subjects as well as for humans. That is, the appended claims are intended to include veterinary uses of the new composition and method according to the invention. Animals also suffer from disorders that are similar to IBD and celiac disease, and the composition of the present invention will be useful for treating such animals The composition that has been discovered for treating a subject having IBD comprises the vitamins and minerals of Table 1, in the range of amounts shown. The metals are to be provided as salts, with the amount of each metal shown being the amount of the elemental metal provided by its salt in the composition.

TABLE 1

| | |
|---|---|
| Vitamin A | 1,500 to 5,000 IU |
| Vitamin D | 200 to 600 IU |
| Vitamin E | 15 to 100 IU |
| Vitamin K | 15 to 60 mcg |
| Vitamin C | 30 to 150 mg |
| Vitamin $B_1$ | 1 to 6 mg |
| Vitamin $B_2$ | 1 to 6 mg |
| Vitamin $B_6$ | 1 to 6 mg |
| Vitamin $B_{12}$ | 150 to 1,000 mcg |
| Folic Acid | 0.2 to 0.5 mg |
| Niacin | 5 to 20 mg |
| Biotin | 0.1 to 0.2 mg |
| Pantothenic acid | 2 to 8 mg |
| Iron | 6 to 20 mg |
| Calcium | 50 to 200 mg |
| Zinc | 5 to 15 mg |
| Selenium | 20 to 50 mcg |
| Copper | 0.5 to 1.5 mg |
| Iodine | 60 to 80 mcg |
| Manganese | 0.5 to 1.5 mg |

The individual vitamins may be included in the composition in more than one form and still be encompassed by the teachings of the invention. For example, vitamin A may be included as retinyl acetate, beta-carotene, retinoic acid, or retinal. Vitamin E may be included as dl-alpha tocopherol acetate, succinate, or phosphate. Vitamin C may be included as ascorbic acid, ascorbate salts, or vitamin C esters. Vitamin $B_1$ may be included as thiamine mononitrate, hydrochloride, monophosphate chloride, or pyrophosphate chloride. Vitamin $B_6$ may be included as pyridoxine hydrochloride or pyridoxal phosphate.

A preferred composition for use according to the teachings of the invention is the embodiment shown in Table 2.

TABLE 2

| | |
|---|---|
| Vitamin A (retinyl acetate) | 2,500 IU |
| Vitamin D (cholecalciferol) | 400 IU |
| Vitamin E (dl-alpha tocopherol acetate) | 75 IU |
| Vitamin K (phytonadione) | 40 mcg |
| Vitamin C (ascorbic acid) | 100 mg |
| Vitamin B1 (thiamine mononitrate) | 5 mg |
| Vitamin B2 (riboflavin) | 5 mg |
| Vitamin B6 (pyridoxine hydrochloride) | 5 mg |
| Vitamin B12 (cyanocobalamin) | 500 mcg |
| Folic Acid | 0.2 mg |
| Niacin (niacinamide) | 10 mg |

TABLE 2-continued

| | | |
|---|---|---|
| Biotin | 0.15 | mg |
| Pantothenic acid | 5 | mg |
| Iron | 15 | mg |
| Calcium | 100 | mg |
| Zinc | 11.25 | mg |
| Selenium | 35 | mcg |
| Copper | 1.0 | mg |
| Iodine | 75 | mcg |
| Manganese | 1.0 | mg |

In a preferred embodiment, the inventive composition comprises mineral salts selected from the group consisting of phosphates, sulfates, and fumarates. It is especially preferred that the inventive composition is essentially free of any carbonate. That is, the composition preferably has no significant amount of carbonate present. This is to avoid the possibility of gas generation within the gastrointestinal tract of a subject receiving the composition.

It is also preferred that the inventive composition is essentially free of magnesium, so as to avoid its cathartic effect. Preferably, the inventive composition is also essentially free of lactose, other sugars, colorants, artificial sweeteners and flavorings. These are also to be avoided to prevent the effects of these substances on the gastrointestinal tract of a subject having IBD or celiac disease.

A method of treating a subject who has an inflammatory bowel disease or celiac disease is also contemplated as being associated with the present invention. The new method may be carried out by providing a composition, as disclosed above, and administering the composition orally to the subject. This method may be carried out by administering the composition in either a solid dosage form, or in a liquid dosage form.

The present invention also includes a method of making a medicament that comprises the new composition disclosed here. This method involves mixing the vitamins and minerals in the amounts disclosed here, where the medicament is intended for use in treating ulcerative colitis, Crohn's disease, or celiac disease. The medicament being made can be in either a solid dosage form, or a liquid dosage form.

The present invention is not to be limited in scope by the embodiments disclosed herein in the Tables, which are intended as single illustrations of one aspect of the invention, and any which are functionally equivalent are within the scope of the invention. Indeed, various modifications of the invention, in addition to those shown and described herein, will become apparent to those skilled in the art from the foregoing description. Such modifications are intended to fall within the scope of the appended claims. All patents and any publications mentioned herein are hereby incorporated by reference.

I claim:

1. A nutritional composition, comprising:

a mixture of vitamins and minerals having the following composition in a pharmaceutically acceptable formulation:

| | | |
|---|---|---|
| Vitamin A | 1,500 to 5,000 | IU |
| Vitamin D | 200 to 600 | IU |
| Vitamin E | 15 to 100 | IU |
| Vitamin K | 15 to 60 | mcg |
| Vitamin C | 30 to 150 | mg |
| Vitamin $B_1$ | 1 to 6 | mg |
| Vitamin $B_2$ | 1 to 6 | mg |
| Vitamin $B_6$ | 1 to 6 | mg |
| Vitamin $B_{12}$ | 150 to 1,000 | mcg |
| Folic Acid | 0.2 to 0.5 | mg |
| Niacin | 5 to 20 | mg |
| Biotin | 0.1 to 0.2 | mg |
| Pantothenic acid | 2 to 8 | mg |
| Iron | 6 to 20 | mg |
| Calcium | 50 to 200 | mg |
| Zinc | 5 to 15 | mg |
| Selenium | 20 to 50 | mcg |
| Copper | 0.5 to 1.5 | mg |
| Iodine | 60 to 80 | mcg |
| Manganese | 0.5 to 1.5 | mg | wherein the minerals are included as salts other than carbonates.

2. The composition according to claim 1, wherein the minerals are included as salts selected from the group consisting of phosphates, sulfates and fumarates.

3. The composition according to claim 1, wherein the iron is present as ferrous fumarate.

4. The composition according to claim 1, wherein the calcium is present as calcium diphosphate.

5. The composition according to claim 1, wherein the composition is essentially free of magnesium.

6. The composition according to claim 1, wherein the composition further comprises a pharmaceutically acceptable excipient selected from the group consisting of: carboxymethylcellulose, microcrystalline cellulose, starch, and modified starch.

7. The composition according to claim 6, wherein the composition is in the form of a unit dosage form selected from the group consisting of: a tablet, a caplet, and a capsule.

8. The composition according to claim 1, wherein the composition is in the form of a liquid unit dosage form.

9. The composition according to claim 1, wherein the mixture has substantially the following amounts of vitamins and minerals:

| | | |
|---|---|---|
| Vitamin A | 2,500 | IU |
| Vitamin D | 400 | IU |
| Vitamin E | 75 | IU |
| Vitamin K | 40 | mcg |
| Vitamin C | 100 | mg |
| Vitamin $B_1$ | 5 | mg |
| Vitamin $B_2$ | 5 | mg |
| Vitamin $B_6$ | 5 | mg |
| Vitamin $B_{12}$ | 500 | mcg |
| Folic Acid | 0.2 | mg |
| Niacin | 10 | mg |
| Biotin | 0.15 | mg |
| Pantothenic acid | 5 | mg |
| Iron | 15 | mg |
| Calcium | 100 | mg |
| Zinc | 11.25 | mg |
| Selenium | 35 | mcg |
| Copper | 1.0 | mg |
| Iodine | 75 | mcg |
| Manganese | 1.0 | mg. |

10. A method for treating a subject having either an inflammatory bowel disease or celiac disease, comprising:

a) administering to a subject, by mouth, a composition in unit dosage form comprising:

| | |
|---|---|
| Vitamin A | 1,500 to 5,000 IU |
| Vitamin D | 200 to 600 IU |
| Vitamin E | 15 to 100 IU |
| Vitamin K | 15 to 60 mcg |
| Vitamin C | 30 to 150 mg |
| Vitamin $B_1$ | 1 to 6 mg |
| Vitamin $B_2$ | 1 to 6 mg |
| Vitamin $B_6$ | 1 to 6 mg |
| Vitamin $B_{12}$ | 150 to 1,000 mcg |
| Folic Acid | 0.2 to 0.5 mg |
| Niacin | 5 to 20 mg |
| Biotin | 0.1 to 0.2 mg |
| Pantothenic acid | 2 to 8 mg |
| Iron | 6 to 20 mg |
| Calcium | 50 to 200 mg |
| Zinc | 5 to 15 mg |
| Selenium | 20 to 50 mcg |
| Copper | 0.5 to 1.5 mg |
| Iodine | 60 to 80 mcg |
| Manganese | 0.5 to 1.5 mg | in a pharmaceutically acceptable formulation, wherein the minerals are included as salts other than carbonates.

11. The method according to claim 10, wherein the iron is present as ferrous fumarate.

12. The method according to claim 10, wherein the calcium is present as calcium diphosphate.

13. The method according to claim 10, wherein the composition is essentially free of magnesium.

14. The method according to claim 10, wherein the composition further comprises a pharmaceutically acceptable excipient selected from the group consisting of: carboxymethylcellulose, microcrystalline cellulose, starch, and modified starch.

15. The method according to claim 10, wherein the composition is in the form of a unit dosage form selected from the group consisting of: a tablet, a caplet, and a capsule.

16. The method according to claim 10, wherein the composition is in the form of a liquid dosage form.

17. The method according to claim 10, wherein the composition has substantially the following amounts of vitamins and minerals:

| | |
|---|---|
| Vitamin A | 2,500 IU |
| Vitamin D | 400 IU |
| Vitamin E | 75 IU |
| Vitamin K | 40 mcg |
| Vitamin C | 100 mg |
| Vitamin $B_1$ | 5 mg |
| Vitamin $B_2$ | 5 mg |
| Vitamin $B_6$ | 5 mg |
| Vitamin $B_{12}$ | 500 mcg |
| Folic Acid | 0.2 mg |
| Niacin | 10 mg |
| Biotin | 0.15 mg |
| Pantothenic acid | 5 mg |
| Iron | 15 mg |
| Calcium | 100 mg |
| Zinc | 11.25 mg |
| Selenium | 35 mcg |
| Copper | 1.0 mg |
| Iodine | 75 mcg |
| Manganese | 1.0 mg. |

18. The method according to claim 10, wherein step a) is carried out twice daily.

* * * * *